(12) United States Patent
Lauer

(10) Patent No.: US 9,789,300 B2
(45) Date of Patent: Oct. 17, 2017

(54) VALVE DEVICE, VALVE INSERT, EXTERNAL FUNCTIONAL MEANS, TREATMENT APPARATUS, AND METHOD

(75) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1578 days.

(21) Appl. No.: 12/766,266

(22) Filed: Apr. 23, 2010

(65) Prior Publication Data

US 2010/0274169 A1    Oct. 28, 2010

Related U.S. Application Data

(60) Provisional application No. 61/185,603, filed on Jun. 10, 2009.

(30) Foreign Application Priority Data

Apr. 23, 2009 (DE) .................. 10 2009 018 664
Jun. 10, 2009 (DE) .................. 10 2009 024 469

(51) Int. Cl.
| | |
|---|---|
| A61M 1/10 | (2006.01) |
| B23P 11/00 | (2006.01) |
| A61M 39/22 | (2006.01) |
| A61M 39/24 | (2006.01) |

(52) U.S. Cl.
CPC ....... *A61M 39/22* (2013.01); *A61M 2039/226* (2013.01); *A61M 2039/2433* (2013.01); *A61M 2039/2446* (2013.01); *A61M 2205/128* (2013.01); *Y10T 29/49826* (2015.01)

(58) Field of Classification Search
USPC .............................. 604/6.1, 137; 251/83, 82
See application file for complete search history.

(56) References Cited

U.S. PATENT DOCUMENTS

| | | | | |
|---|---|---|---|---|
| 3,889,710 | A | * | 6/1975 | Brost .................... F16K 15/141 |
| | | | | 137/512.15 |
| 3,941,149 | A | | 3/1976 | Mittleman |
| 4,712,583 | A | * | 12/1987 | Pelmulder ............. A61M 39/24 |
| | | | | 137/494 |
| 4,815,705 | A | | 3/1989 | Kasugai et al. |
| 4,819,684 | A | * | 4/1989 | Zaugg .................. A61M 39/02 |
| | | | | 137/112 |

(Continued)

FOREIGN PATENT DOCUMENTS

| | | |
|---|---|---|
| DE | 100 53 441 A1 | 5/2002 |
| DE | 10 2009 012 632.5 | 9/2010 |

(Continued)

OTHER PUBLICATIONS

PCT International Search Report for PCT/EP2010/002295, mailed on Sep. 19, 2010.

(Continued)

*Primary Examiner* — Tatyana Zalukaeva
*Assistant Examiner* — Guy K Townsend
(74) *Attorney, Agent, or Firm* — Fish & Richardson P.C.

(57) ABSTRACT

The present invention relates to a valve device comprising an elastic valve insert and a reception means for the valve insert. It further relates to a valve insert, an external functional means and a treatment apparatus, as well as a manufacturing method and methods in which the valve device of the invention may be employed.

27 Claims, 7 Drawing Sheets

(56) References Cited

U.S. PATENT DOCUMENTS

| | | | | |
|---|---|---|---|---|
| 4,946,448 A * | 8/1990 | Richmond | ............ | A61M 39/24 137/493.9 |
| 5,186,431 A * | 2/1993 | Tamari | ................ | A61M 1/0031 251/5 |
| 5,306,265 A * | 4/1994 | Ragazzi | ................ | A61M 39/02 128/912 |
| 5,462,256 A * | 10/1995 | Minick | ............. | A61M 5/14224 251/331 |
| 5,775,671 A * | 7/1998 | Cote, Sr. | ............... | F16K 15/185 251/149.1 |
| 5,776,118 A * | 7/1998 | Seifert | .................. | A61L 11/00 422/292 |
| 6,039,724 A * | 3/2000 | Seifert | .................. | A61L 11/00 604/533 |
| 6,196,987 B1 * | 3/2001 | Holmes | ............... | A61M 1/3624 494/18 |
| 6,200,287 B1 * | 3/2001 | Keller | ................ | A61M 1/3693 210/767 |
| 6,390,120 B1 * | 5/2002 | Guala | .................. | A61M 39/24 137/512.15 |
| 6,537,258 B1 * | 3/2003 | Guala | .................. | A61M 39/24 137/522 |
| 6,554,789 B1 * | 4/2003 | Brugger | .................. | A61M 1/34 210/252 |
| 6,579,253 B1 * | 6/2003 | Burbank | ................ | A61M 1/34 210/252 |
| 6,595,943 B1 * | 7/2003 | Burbank | ................ | A61M 1/34 210/257.2 |
| 6,638,477 B1 * | 10/2003 | Treu | ....................... | A61M 1/34 210/252 |
| 6,638,478 B1 * | 10/2003 | Treu | ....................... | A61M 1/34 210/252 |
| 6,830,553 B1 * | 12/2004 | Burbank | ................ | A61M 1/34 210/321.6 |
| 6,852,090 B2 * | 2/2005 | Burbank | ................ | A61M 1/34 210/252 |
| 6,899,693 B2 * | 5/2005 | Ghelli | .................. | A61M 1/1037 604/6.1 |
| 7,147,613 B2 * | 12/2006 | Burbank | ................ | A61M 1/34 210/257.2 |
| 7,153,286 B2 * | 12/2006 | Busby | .................... | A61M 1/28 210/252 |
| 7,169,352 B1 * | 1/2007 | Felt | ..................... | A61M 1/0209 210/645 |
| 7,238,164 B2 * | 7/2007 | Childers | ................ | A61M 1/284 210/258 |
| 7,267,658 B2 * | 9/2007 | Treu | ....................... | A61M 1/34 210/646 |
| 7,300,413 B2 * | 11/2007 | Burbank | ................ | A61M 1/34 210/252 |
| 7,338,460 B2 * | 3/2008 | Burbank | ................ | A61M 1/34 210/645 |
| 7,347,849 B2 * | 3/2008 | Brugger | .................. | A61M 1/34 210/645 |
| 7,473,238 B2 * | 1/2009 | Brugger | .................. | A61M 1/34 210/645 |
| 7,503,348 B2 * | 3/2009 | Irwin | ....................... | F16K 7/17 137/625.68 |
| 7,556,060 B2 * | 7/2009 | Guala | .................. | A61M 39/24 137/599.03 |
| 7,610,936 B2 * | 11/2009 | Spohn | .................. | A61M 5/007 137/877 |
| 7,641,174 B2 * | 1/2010 | Enerson | ................ | F16K 15/141 137/859 |
| 7,981,090 B2 * | 7/2011 | Plishka | ............... | A61M 39/045 604/246 |
| 2002/0103453 A1 * | 8/2002 | Burbank | ................ | A61M 1/34 604/4.01 |
| 2004/0019313 A1 | 1/2004 | Childers et al. | | |
| 2004/0238416 A1 * | 12/2004 | Burbank | ................ | A61M 1/34 210/85 |
| 2004/0243047 A1 * | 12/2004 | Brugger | .................. | A61M 1/34 604/4.01 |
| 2004/0243048 A1 * | 12/2004 | Brugger | .................. | A61M 1/34 604/4.01 |
| 2004/0243049 A1 * | 12/2004 | Brugger | .................. | A61M 1/34 604/4.01 |
| 2004/0243050 A1 * | 12/2004 | Treu | ....................... | A61M 1/34 604/4.01 |
| 2004/0245161 A1 * | 12/2004 | Treu | ....................... | A61M 1/34 210/110 |
| 2004/0249331 A1 * | 12/2004 | Burbank | ................ | A61M 1/34 604/4.01 |
| 2004/0267184 A1 * | 12/2004 | Burbank | ................ | A61M 1/34 604/6.11 |
| 2005/0010158 A1 * | 1/2005 | Brugger | .................. | A61M 1/34 604/6.09 |
| 2005/0020959 A1 * | 1/2005 | Brugger | .................. | A61M 1/34 604/4.01 |
| 2005/0020960 A1 * | 1/2005 | Brugger | .................. | A61M 1/34 604/4.01 |
| 2005/0045548 A1 * | 3/2005 | Brugger | .................. | A61M 1/34 210/252 |
| 2005/0153430 A1 * | 7/2005 | Ohtaka | ............. | B01L 3/502738 435/287.2 |
| 2005/0209563 A1 * | 9/2005 | Hopping | .................. | A61M 1/28 604/151 |
| 2005/0234385 A1 * | 10/2005 | Vandlik | ............... | A61M 1/1037 604/6.03 |
| 2005/0257837 A1 * | 11/2005 | Bailey | .................... | A61M 39/24 137/512.15 |
| 2005/0267418 A1 | 12/2005 | Fournie et al. | | |
| 2006/0079827 A1 * | 4/2006 | Jensen | ................ | A61M 39/223 604/6.1 |
| 2006/0108008 A1 * | 5/2006 | Guala | .................. | A61M 39/24 137/605 |
| 2006/0178612 A9 * | 8/2006 | Vandlik | ............... | A61M 1/1037 604/6.03 |
| 2006/0293734 A1 * | 12/2006 | Scott | ....................... | A61F 7/12 607/105 |
| 2007/0060872 A1 * | 3/2007 | Hall | ................... | A61B 5/14546 604/66 |
| 2007/0161970 A1 * | 7/2007 | Spohn | .................... | A61M 5/007 604/533 |
| 2007/0179436 A1 * | 8/2007 | Braig | .................... | A61B 5/145 604/66 |
| 2007/0232980 A1 * | 10/2007 | Felt | ..................... | A61M 1/0209 604/6.1 |
| 2007/0278155 A1 * | 12/2007 | Lo | ........................... | A61M 1/16 210/646 |
| 2008/0058720 A1 * | 3/2008 | Spohn | .................. | A61M 5/007 604/140 |
| 2008/0077068 A1 * | 3/2008 | Orr | .......................... | F04B 7/02 604/6.11 |
| 2008/0154214 A1 * | 6/2008 | Spohn | .................. | A61M 5/007 604/247 |
| 2008/0185062 A1 | 8/2008 | Johannes Nijland | | |
| 2008/0215015 A1 * | 9/2008 | Cindrich | ............ | A61M 5/14248 604/257 |
| 2008/0306426 A9 * | 12/2008 | Brugger | .................. | A61M 1/34 604/6.11 |

FOREIGN PATENT DOCUMENTS

| | | |
|---|---|---|
| DE | 10 2009 012 633.3 | 9/2010 |
| DE | 10 2009 018 664.6 | 10/2010 |
| EP | 1 661 599 A1 | 5/2006 |
| EP | 1 946 793 A1 | 7/2008 |
| EP | 1 953 432 A2 | 8/2008 |
| JP | 51-070530 | 6/1973 |
| JP | 63-135670 | 6/1988 |
| JP | 05-507015 | 9/1992 |
| JP | 2001129080 | 5/2001 |
| JP | 2001252362 | 9/2001 |
| JP | 2002177383 A | 6/2002 |
| JP | 2006500076 A | 1/2006 |

(56) References Cited

FOREIGN PATENT DOCUMENTS

| | | |
|---|---|---|
| JP | 2007117210 | 5/2007 |
| JP | 2008500070 | 1/2008 |
| WO | 2005/116497 A1 | 12/2005 |

OTHER PUBLICATIONS

Japanese Search Report in Japanese Application No. 2012-506375, dated Feb. 19, 2014, 23 pages (with English translation).

* cited by examiner

VALVE DEVICE, VALVE INSERT, EXTERNAL FUNCTIONAL MEANS, TREATMENT APPARATUS, AND METHOD

RELATED APPLICATIONS

This application claims the benefit of U.S. Provisional Patent Application No. 61/185,603, filed on Jun. 10, 2009, which is expressly incorporated herein in its entirety by reference thereto. Further, this application claims priority to German Patent Application No. 10 2009 018 664.6, filed on Apr. 23, 2009, and German Patent Application No. 10 2009 024 469.7, filed on Jun. 10, 2009, each of which is expressly incorporated herein in its entirety by reference thereto.

FIELD OF THE INVENTION

The present invention relates to a valve device. It further relates to a valve insert, an external functional means, as well as a method for controlling or regulating a passage of fluid. It furthermore relates to a method of manufacturing a valve device, a method of manufacturing an external functional means, a method for preparing an external functional means for sterile utilization, an external functional means for sterile utilization, as well as a treatment apparatus.

BACKGROUND

For reasons of costs and hygiene, external functional means are frequently employed as single-use part systems such as, for example, disposable cassettes in technical apparatuses such as, for example, medical-technical treatment apparatuses, laboratory-technical apparatuses, or also apparatuses for food or drug production.

Such single-use part systems may comprise passages and chambers for intentionally conducting liquids and gases, as well as apparatuses such as valve devices for varying or controlling the passage of these fluids.

It is an object of the present invention to provide another device for such single-use part systems or other apparatuses. Furthermore, it is intended to provide a corresponding valve insert, an external functional means, and corresponding methods.

SUMMARY

The valve device of the invention comprises at least one valve insert that is elastic in at least one portion thereof, and at least one reception means for the valve insert.

The valve insert of the valve device of the invention is provided and configured in such a way that it may be switched or changed over between at least three different valve states upon impression of path and/or application of force to the valve insert or to some other portion of the valve device. The "switching capability" of the valve insert shall, in the broadest meaning, in the following be understood to be the capability to obtain at least three valve states by means of the valve insert.

In accordance with the invention, an "impression of path" is preferably understood to be an alteration of a variable dimension of a structure or of a component part. Thus, in the case of a spiral spring a impression of path may designate its elongation or compression. When applied to the valve insert of the valve device of the invention, an impression of path designates its compression, extension, deformation, and the like.

The expression "valve insert" as presently used designates the base body of the valve device of the invention that is deformable due to its elasticity. During its use, the valve insert is entirely or partly flushed by the fluid flow, but is, however, at least in contact with fluid when a fluid is present at the valve device.

A "reception means" for the valve insert as presently used designates a reception means configured and/or intended for receiving the valve insert.

Such "receiving" may effect embracing, supporting, establishing a functional relationship between the reception means and the valve insert, and the like.

Some of the features given in the following may be features of the valve device of the invention or of its valve insert. Independently of or in combination with other features, these features may be realized in any embodiment.

The reception means may include an opening suited for receiving the valve insert.

The valve insert may in particular owe its switching capability between at least three different valve states to its elasticity.

In accordance with the invention, the valve insert may be configured to change over to various valve states, or enable these valve states, solely by its elastic deformation or elastic release or elastic deformability.

An alteration of the position of the valve portion or of a portion thereof relative to, for example, a portion of the valve device such as the reception means which is not part of the valve portion, may be unnecessary for switching between the valve states.

Due to the force, the valve insert may undergo an elastic—i.e., reversible—deformation; for example it may curve, fold, bend, or the like. Depending on impression of path and/or application of force applied to the valve insert, it may thus adopt different valve states. The reset forces resulting from the elastic deformations may effect functions such as protection against falling out, self-releasing, sealing, and/or response pressure.

The valve insert may be symmetrical. It may, for example, have a rotationally symmetrical shape.

The reception means may be adapted and/or provided to receive the valve insert substantially accurately fitting and/or to keep it under installation bias or stress.

It may be adapted and/or provided to admit tolerances during assembly and/or pressing of the valve insert.

The reception means may be produced of one or several inelastic materials such as, for example, duroplastic or thermosetting plastics, metals and the like, as well as combinations thereof.

The rigidity of the reception means may preferably be substantially higher than that of the valve insert. The flexural strength and/or the compressibility of the valve insert can, for example, be 60 N/mm$^2$ to 300 N/mm$^2$, and those of the reception means can, for example, be 800 N/mm$^2$ to 2400 N/mm$^2$.

The reception means may be disposed in a housing element such as, for example, a hard part of, for example, an external functional means such as, for example, a disposable cassette. It may, for example, be formed inside a housing element of an external functional means—for instance upon manufacturing the external functional means.

An "external functional means" may be a fluid treatment cassette or a tube installation element. A fluid treatment cassette, blood treatment cassette or disposable cassette within the meaning of the present invention is, for example, disclosed in German Patent Application Nos. 10 2009 018 664.6 (representative's file FM19A27) and 10 2009 024

468.9 (09/33-d01 DE; FM19B27) each having the title "Externe Funktionseinrichtung, Blutbehandlungsvorrichtung zum Aufnehmen einer erfindungsgemäßen externen Funktionseinrichtung, sowie Verfahren" [External functional means, blood treatment apparatus for receiving an external functional means in accordance with the invention, and method] filed at the German Patent and Trademark Office on Apr. 23, 2009 and on Jun. 10, 2009 by the applicant of the present invention, the respective disclosures of which are herewith fully incorporated by way of reference thereto. A preferred embodiment of the blood cassette as disclosed therein is represented in FIGS. 8, 9, and 10 of the present application.

The expression "housing element" as presently used designates a component that may be part of an external functional means, of a treatment apparatus and/or both of the external functional means and of the treatment apparatus.

The housing element may be formed of a rigid, i.e., substantially inelastic material.

The housing element of an external functional means may fulfil various functions. Without being restricted to this, it may constitute a fluid passage, a sealing seat of the valve insert, e.g. as a separation between an inflow passage and an outflow passage for fluids passing through the valve device, such as blood or substitute liquid or a sterilizing fluid (a liquid and/or a gas) or a rinsing liquid.

The housing element may serve as a mount for the valve insert, ensure correct axial displacement or pressing of the valve insert, and the like. The indefinite articles "a" and "an" should here and in the entire application not be understood to be a limitation or a numeral either.

The housing element may include passages such as inflow and outflow passages through which fluids are introduced into the valve device or discharged therefrom. Such passages may be configured as semi-open or as closed passages. They may, for example, also be configured as semi-open passages in one portion and closed passages in another portion.

Closed passages may in particular be suited as a transition to directly coupled connector elements such as, for example, Luer connectors or tubing sleeves.

Semi-open passages may in particular be preferred in external functional means such as, for example, a disposable cassette. The use of semi-open passages in an external functional means may allow for high freedom of design in the "fluid layout", for example by forming guiding means or branchings leading to measurement and/or venting chambers.

Passages that are provided in the housing element, for instance inflow passages leading into the valve device and/or outflow passages leading out of the valve device, may be realized at an arbitrary angle to each other. This may be an angle of precisely or approximately 180 degrees or also an angle of less than 90 degrees. Preferably, the angle may take a value in a range from 45 degrees to 315 degrees.

A coaxial arrangement of the passages with an axis of symmetry of the valve insert—which is optionally present—may also be realized. Such an arrangement may be preferred. This is particularly preferred if the valve insert is not placed or inserted, for instance, in an external functional means but is placed or inserted in a tube conduit as a so-called in-line functional element.

If, for example, both flow passages are intended to be aligned coaxially with the valve insert, interruptions may be formed in the seat region of the housing element, which permit axial flushing of the fluids passing through the valve device around the valve insert.

In such a case, openings in a bending ring region of the valve insert are preferably provided. Housing members may then be configured in a particularly reduced installation space, e.g., with small diameters. Overall, the valve device may be designed in a rheologically efficient manner.

By means of stepped impression of path and/or application of force, for instance by means of an actor on an upper side of the valve insert, the valve insert may be taken into various defined states of deformation. Depending on the force applied to the valve insert and/or the impression of path, particular valve functions or valve states or valve positions may be realized. In some or all of these valve states the valve insert may be subjected to an elastic tension.

A valve state may be an opened or open valve state.

The valve insert, or the valve device, is in an opened or open valve state whenever no external force is applied to the valve insert. Thereby, the valve insert may be inserted in the reception means. In this condition the valve insert may be free of any bias or pre-load and/or twisting generated between components.

The passage of fluids may be maximum in this condition. Passage openings for fluids passing through the valve insert may in this state be opened to maximum.

One valve state may be a sterilization state.

For sterilization of the valve device or of an external functional means comprising a valve device of the invention, the valve insert will preferably be present in the sterilization state.

In the sterilization state, the valve insert may preferably have or adopt the same configuration or shape as in the opened valve state.

In the sterilization state, the valve insert may in turn be free of external forces and/or bias or pre-load and/or twisting with other components such as, for example, the reception means, and/or be free of any impressions of path.

In the sterilization state, a bidirectional passage of fluids through the valve device may be possible.

In the sterilization state, the sterilization agent may preferably reach all of the volumes and partial volumes, openings, undercuts, etc. of the valve device that are accessible in terms of construction technology.

Another valve state may be a check valve state.

A check valve is known from the prior art, for example as a spherical or cylindrical sealing body in combination with biased springs. A check valve may equally act as a pressure relief valve.

The "check valve state" of the valve insert or of the valve device of the present invention may serve for determining the direction of flow of a fluid inside one or several flow passages.

In the check valve state, the passage of a fluid may be blocked in one direction of flow.

Another valve state may be a control or regulating valve state.

In the control or regulating valve state, a force which is preferably variable is applied to the valve insert of the valve device, whereby a flow rate of the fluids passing through the valve device may be controlled or regulated.

To this end the valve device may, for example, be driven actively by actors transmitting forces and/or movements.

Suitable actors may, for example, be coupled to a treatment apparatus and may in particular be operated or controlled/regulated by the latter.

The absolute force to be applied to the valve insert and/or the impression of path to be applied for controlling or regulating, for instance in order to adjust a particular or defined flow rate, may be set as a function of the desired or required flow rate of the fluids passing through the valve device.

It may, for example, be pre-programmed in a control means, a CPU, or the like.

The force and/or the impression of path (displacement) may be applied via actors, for instance on the upper side of the valve insert.

Another possible valve state is a closed valve state.

In the closed valve state, the flow rate of the fluids passing through the valve device may be reduced such that a passage does not or substantially does not take place.

The valve insert may be disposed such that the openings provided for the passage of fluids are substantially inaccessible or closed. The openings may be entirely inaccessible or closed.

The valve state may be a permanently closed valve state.

The valve insert may entirely or at least in portions thereof have a rotationally symmetrical configuration.

In a further preferred embodiment, the valve insert comprises an elastomer material in at least one portion thereof. The valve insert may be configured to be elastic as a whole or at least in portions thereof.

Suitable elastomer materials include—without being restricted thereto—rubber, silicone, TPE (thermoplastic elastomers), TPE-U (occasionally also abbreviated as TPU; thermoplastic elastomers on the basis of polyurethane), plastics, PVC, and the like.

Liquid-crystalline elastomers and/or thermoplastic elastomers may also rank among the suitable elastomer materials.

Thermoplastic elastomers may preferably be mixtures of one or more elastomers and one or more thermoplastic materials.

Such thermoplastic materials may be suited, for instance, for the manufacture of rigid housing elements of an external functional means.

The thermoplastic elastomers may be bonded and/or welded and/or may in some other manner be connected frictionally and/or by form closure and/or by material connection to injection-molded housing elements.

The valve insert may have impressions in the sense of portions of thinner or softer materials as compared with other portions thereof, which may ensure a particular elasticity or deformability thereof. Such impressions may be configured by pressure by means of rollers, rolls, dies and the like, but also during casting or extruding operation.

The valve insert may have a predetermined folding pattern or a creased or folded portion that, following an extension, may elastically be released into an initial position.

The valve insert may be configured as a single-component valve insert, but also as a multi-component valve insert.

In a further preferred embodiment, the valve insert may include at least one first sealing means provided and configured to be adapted for being pressed in form closure and/or frictional connection in at least one portion thereof with at least one portion of a second sealing means of the reception means.

The "first sealing means" may be an elastic sealing ring. It may be a peripheral, in particular closed, sealing lip. The sealing lip may have, e.g., a planar shape, a conical shape, and/or a slightly undulating shape.

Depending on a state of deformation of the valve insert, the first sealing means may rest on a defined sealing surface at the reception means, for instance the second sealing means, or on the valve insert.

The first sealing means may have a disc shape or be disc-shaped. The first sealing means may be biased via an axial center, for instance in a central region of a disc-shaped first sealing means. The central region may be an inner region. Preferably, the central region is a region of an accumulation of material or of a "core."

The "second sealing means" may be a rigid sealing ring.

The second sealing means may be provided on the valve insert or on the reception means, furthermore also on some other means.

The second sealing means may have a slightly undulating shape but may also have a planar shape.

Due to the axial bias or pre-load of the first sealing means of the valve insert, an adaptation of the first sealing means to the shape of the second sealing means may take place.

Such an adaptation may preferably effect a sealing effect.

In a check valve state this sealing effect may further be enhanced by the fluid pressure. The first sealing means may be pressed more strongly against the second sealing means. Similarly, the shape of the second and/or of the first sealing means possibly deviating from the ideal planar shape may be adapted to the shape of the elastic disc of the first sealing means by means of a surface load acting on the elastic disc.

The first sealing means and the second sealing means may ensure a required compensation of geometrical tolerances.

Such a compensation of tolerances may take effect through the capability of the first sealing means to perform an angular and/or bowl-type flexure under the influence of bias and/or fluid pressure.

A compensation of geometrical tolerances may also take effect in the case of an axial tolerance in the generation of the bias or in the case of an angular tolerance or deviation between the axis of symmetry of the seat topology of the reception means and of the axis of symmetry of the valve insert.

A lateral tolerance possibly existing between the two axes may be compensated by the first sealing means having a diameter overlap with the second sealing means. In this way a sealing effect within the area of overlap may be ensured.

Another function of the arrangement for compensating tolerances may consist in shunting out minor irregularities, notches and/or roughnesses in the sealing upper sides of the two sealing means, wherein the bias in combination with the effective area of contact may be selected such as high as to result in a local deformation of the first sealing means, wherein faults such as irregularities, notches, roughnesses and the like will thus be filled with the elastic material and thereby result in a tight closure.

Depending on the configuration, during use a sufficient surface pressure may be build up between the first and second sealing means at the annular zone of contact or pressing.

As illustrated in the appended figures, in the most simple case, a planar or substantially planar shape of the first sealing means may be provided in the zone of seal in combination with a tapered shape of the second sealing means.

On the contrary, the pointed element of such a geometrical match suitable for levelling may also be a pointed annular sealing bar at the first sealing means, which may rest under bias on the hard second sealing means that will in this case be flat or slightly curved or conical.

The correlation of pointed and flat structures may preferably result in the high surface pressure required for levelling and thus ensure all kinds of compensation of tolerances mentioned above.

The functions of sealing and compensation of tolerance may not only be realized in the case of a flat configuration of the sealing means. They may equally be achieved if the sealing means are intentionally and/or by means of axial bias deformed into a bowl-type or conical shape.

At least one of the sealing means involved may therefore be designed in the shape of a pointed peripheral bar. In this way a tolerance or immunity against the different conical and/or bowl-type shape in the state of pressing or sealing may result. This may also be referred to as a semi-axial sealing mode as compared to an exclusively axial sealing mode.

The advantages of the compensation of lateral tolerances may fully be preserved here as compared to an exclusively radial sealing mode.

In a further preferred embodiment, the first sealing means is adapted to be pressable with the second sealing means by means of transmission of force and/or impression of path to the valve insert, or is pressed during use.

The expression "pressing" as presently used designates a frictional and/or form closure physical connection of the first sealing means of the valve insert and of the second sealing means of the reception means.

The transmitted force may be a force that is supplied or applied from outside. The impression of path may be an alteration of path or a displacement supplied or applied from outside.

In a further preferred embodiment, the force acting on the valve insert is a pressing force introducable by installation of the valve device into a treatment apparatus.

In a further preferred embodiment, the impression of path to the valve insert is a displacement introducable by installation of the valve device into a treatment apparatus.

The valve device may be provided at an external functional means. The pressing force and/or the impressed pressing path may be introduced, for instance, by pressing the external functional means with the treatment apparatus. Suitable embodiments and methods for pressing an external functional means with a treatment apparatus are described, for example, in German Patent Application Nos. 10 2009 012 633.3 (representative's file FM19A24) having the title "Vorrichtung zum Verbinden einer externen Funktionseinrichtung mit einer Anordnung, Anordnung aufweisend eine solche Vorrichtung und Verfahren zum Verbinden" [Device for connecting an external functional means to an arrangement, arrangement including a like apparatus, and connecting method] and 10 2009 012 632.5 (representative's file FM19A25) having the title "Abdichtungseinrichtung zum Abdichten eines Volumens einer medizinischen Behandlungsanordnung gegen ein weiteres Volumen sowie Anordnung und Verfahren" [Sealing means for sealing a volume of a medical treatment arrangement against another volume, as well as arrangement and method], both of which were filed at the German Patent and Trademark Office on Mar. 10, 2009 by the present applicant. Their respective disclosures are herewith fully incorporated by way of reference thereto.

In a further preferred embodiment, the pressing force and/or the pressing path may be transmitted by a transmission member of the treatment apparatus by using suitable means.

A like "transmission member" may exert functions of pressing and/or (static) sealing of the fluid system and/or the function of introducing forces and actuation movements.

The transmission member may, for example, be a rubber mat. It may be a direct coupling mate for coupling the treatment apparatus to the external functional means.

The transmission member may be subjected to a bowl-type deformation and deflected by application of control fluids or by coupling tappets.

The deformation or deflection of the transmission member may be transmitted to a front ring region of the valve insert.

The transmission member may include a movement transmission means, for instance an axial movement transmission means. An axial movement transmission means may, for example, be disposed centrally above a valve insert, to transmit a force applied to the transmission member and/or a displacement to the upper side of the valve insert.

The transmission member may comprise a coupling surface of elastomer material, so as to be able to achieve sealing and/or tolerance compensation functions between the reception means and/or the external functional means and the treatment apparatus. The counteracting force to the pressing force may be received by a counterpart of the treatment apparatus that supports the end face of the reception means.

It may also be possible to provide an end face region of the valve insert to achieve the functions of the transmission member of the treatment apparatus. For instance, such an end face region may be in direct contact with a tappet (movable or stationary). The end face region may transmit the desired forces and actuation paths into the fluid-functional regions of the valve insert.

Suitable mechanisms are disclosed, for example, in the above-mentioned applications of the present applicant, the respective disclosures of which are herewith fully incorporated by way of reference thereto.

In a further preferred embodiment, the valve insert comprises at least one guiding means for introduction of the valve insert into the reception means.

Such a "guiding means" may be a guide rib, a guide rail, a pulling and/or pushing mechanism, and the like.

In a further preferred embodiment, the valve insert may include at least one bending ring region. The bending ring region may be elastic.

Like the guiding means, the bending ring region may ensure the axial mobility of the valve insert relative to the reception means while providing geometrical centering between the two axes of symmetry.

As it may, however—similar to the deformation of the first sealing means—be a matter of an elastic deformation due to an axial force and/or displacement required for this purpose, a preferential position may result for the valve device which may be adopted automatically if the application of path and forces externally introduced by the treatment apparatus are omitted.

This preferential position may be of crucial importance for the main functions of the valve device.

The bending ring region may exert functions of smoothing or compensating tolerances. It may be possible to systematically install the valve element at a greater axial depth in the reception means. In this way, it is advantageously possible to make up for tolerances of installation depth as the valve insert is capable of returning to the preferential position by itself.

The bending ring region may have a front ring region. The front ring region of the valve insert may have an outer front ring region, an inner front ring region, an front end stop, and a deformation space, for example an annular deformation space.

The outer front ring region may provide a correct target position of the valve insert in the reception means.

In order to ensure an ample diameter tolerance and an ample lateral installation tolerance, the outer front ring region may preferably be configured to be conical at the circumference. It may have a sufficient radial compressibility.

Advantageously, it is thus possible to obtain a non-critical installation situation and in addition a highly accurate, radial and axial centering free from play in the final mounting position.

In combination with the front end stop, the inner front ring region may fulfil a (important) function of compensating tolerances between the treatment apparatus and the external functional means. The relatively lower resilience of the range of material between the front end stop and the first sealing means may, in combination with the relatively high axial resilience of the inner front ring region, ensure that the axial bias between the treatment apparatus and the external functional means may be selected such that the front end stop is arrested at a lower end face of the seat bush of the reception means, while the inner front ring region is capable of absorbing the axial installation tolerances by deformation. In this way, the correct relative position of the regions relevant for the main functions of the valve insert relative to the sealing seat region of the reception means may be ensured.

An axial material distance or a material portion between the outer and the inner front ring region may be sufficiently elastic for absorbing different installation dimension tolerances and pressing forces between the treatment apparatus and the external functional means. This may advantageously be realized without affecting the conditions relevant for the main functions of the proper valve insert.

Optionally, the outer bending ring region of the valve insert may, together with a suitable bending ring region of the valve insert, in a suitable configuration of the static sealing seat of the reception means (selection of diameter and possibly additional provision with static, peripheral sealing bars), also fulfil radial and/or axial sealing functions. This is particularly advantageous if, for example, no other cover means such as, for example, a film element, will be provided between the valve device and the treatment apparatus.

The annular deformation space, for example an annular gap, may be present between the first sealing means, for instance a peripheral sealing lip, and a shaft of the valve insert.

A fluid may flow through the annular deformation space when the first sealing means is not resting on any sealing surface.

The annular deformation space may advantageously permit to reduce the axial installation space for the valve insert. In addition, the annular deformation space may provide additional areas of passage for the fluids and allow for a distribution at low pressure loss of the fluids from the flow passage to the entire ring region of the sealing seat. Hereby, the entire potential open cross-section of the valve device may be utilized.

The valve insert may further comprise a valve seat, for example a static valve seat, and a seat region, preferably an elastic seat region.

The valve insert may be disposed in a cylindrical or substantially cylindrical inner space which may be an integral part of the injection-molded hard part of an external functional means in form of a recess.

The valve insert may, for instance, be retained in a cylindrical or substantially cylindrical seat arrangement of the reception means comprising a lower seat bush and an upper seat bush. Such a geometrical constellation may in particular provide various options for connection of the flow passages.

A guiding means having, for example, the form of a plurality of guide ribs, may have a slight overdimension relative to the diameter of the lower seat portion of the reception means and/or a star-type conformation and/or a spherical conformation.

The star-type conformation may ensure a correct middle centering of the valve insert. It may further ensure free access of the fluids to the sealing seat region at arbitrarily rotated installation positions of the valve insert.

Thus, the valve device may be installed axially in the reception means without being subject to any requirements of rotary positioning.

Due to a low wall thickness of the guide ribs, the valve insert may be relatively resilient against radial compression. In this way, a high diameter tolerance relative to the lower seat bush may be realized.

It is possible to achieve a—preferably homogeneous—low clamping or pressing force which may advantageously ensure that the valve insert cannot fall out from its seat region during the manufacturing process of the external functional means.

On the other hand, the clamping force may be so low that that there will not result any manipulation or distortion of the axial forces or any impediment to the desired displacement movements during subsequent use of the valve device.

Advantageously, the clamping force may even reduce to a large degree during a sterilization treatment and during the storage period of the valve device or of the external functional means until its utilization.

A spherical conformation of the guide ribs may provide at least two further functions. During assembly, the spherical tapered silhouette may form a amply slope of introduction, so that installation may advantageously be performed in a secure manner by means of manual and/or machine installation operations even in the presence of large lateral tolerances. On the other hand, the spherical shape may ensure universal angular mobility between the axes of symmetry of the reception means and of the valve insert.

It is therefore advantageously possible to avoid any material stresses and/or any undesired changes of shape of the elastic sealing ring region upon given tolerances in the conformation of reception means and valve insert that might affect the sealing or opening capabilities of the valve device.

In a further preferred embodiment, the valve device is provided with a cover means on at least one upper side.

The cover means may be bonded, welded, soldered, riveted, etc. to the upper side of the housing element of the reception means.

The cover means may be a film element. It may be a resilient film.

Films are cost-efficient and mechanically resilient. They allow a low-cost realization of valve locations inside a fluid system having one or more locations of interaction by the treatment apparatus in order to effect valve positioning movements.

Instead of the films, it is possible to use elastomer valve switching mats that are inserted, injected in the two-component technique, or fitted in some other manner for initiating the required movements. Likewise, a combination of hard parts, films and/or elastomer bodies is encompassed by the present invention.

The cover means may constitute fluid passages, maintain the valve insert in an axial dimension or direction, close the fluid system in a fluid-tight manner against the outside in combination with permissivity for axial control movements to the valve insert, and transmit pressing forces for controlling or regulating the valve insert and for sealing the reception means or the external functional means, respectively.

The cover means may close off or seal the fluid passage system of the reception means by pressing against the static sealing bar of the reception means. Thereto—or for this purpose—a static sealing bar having, for example, the form of a linear dent may be formed.

The film element may possess sufficient elastic resilience, for instance due to elastic material properties and/or appropriate bellows impressions. Due to the bellows impressions, as predominantly only bending stresses occur in a locally defined manner, the bellows impressions advantageously allow—for example in configurations of the film element as a scroll membrane or scroll bellows—to prevent or at least noticeably reduce the tensile stresses frequently occurring in the membrane plane with planarly tensioned prior art membranes subjected to flexural strains.

Due to the elastic properties of the cover means, the function of the mechanical transmission of movement and/or force from the treatment apparatus to the valve insert may also be ensured in parallel with, or alternatively to, the static sealing function.

In a further preferred embodiment, the valve insert can therefore be switched across the cover means by a force or a displacement transmitted from the treatment apparatus.

Depending on the application, the cover means may alternatively also be omitted. For instance, the valve insert may be sealed against the reception means by welding or by pressing and may thereby additionally provide the functions of sealing and of transmission of movement to the treatment apparatus.

This may advantageously be realized in a particularly simple manner if both flow passages are designed as closed passages. Similarly, in applications with e.g. reduced demands for freedom of the fluid system as regards impurities and/or germs, the transmission member pertaining to the treatment apparatus can additionally fulfil the functions of the cover means.

The object of the invention is further achieved through a valve insert which may be employed in a valve device in accordance with the foregoing description.

A like valve insert may form the core element of the valve device of the invention. Depending on the functional mode or valve state, its main function may consist in opening or closing a flow passage by means of an axial stroke movement of the entire valve insert in the case of the valve states (e.g., sterilization, open, close), or by a deformation such as a flexure under the influence of the fluid (e.g., check valve, control/regulating valve).

In order to achieve the object of the invention, there is further proposed an external functional means comprising at least one valve device in accordance with the invention.

Such an external functional means may, for example, be employed for an extracorporeal blood treatment. The external functional means may be a disposable cassette as described in the German Patent Applications having the title "Externe Funktionseinrichtung, Blutbehandlungsvorrichtung zum Aufnehmen einer erfindungsgemäßen externen Funktionseinrichtung, sowie Verfahren" [External functional means, blood treatment apparatus for receiving an external functional means in accordance with the invention, and method]" filed at the German Patent and Trademark Office by the present applicant, as was stated in the foregoing. The respective contents thereof are herewith fully incorporated by way of reference thereto.

As all of the advantages discussed in connection with the valve device of the invention or mentioned in the following advantages may be transposed in an undiminished manner to the valve insert and/or the external functional means, reference is made to the corresponding explanations in order to avoid repetitions.

The present invention further proposes various methods wherein a valve device of the invention may advantageously be utilized.

A method in accordance with the invention is a method of controlling or regulating a fluid passage, which includes the use of a valve device of the invention.

The expression "fluid passage" may be understood to be a fluid passageway, a fluid flow, a stream of fluid, or the like.

"Control or regulation" of a passage of fluid includes—without being restricted thereto—control or regulation of a velocity, a pressure, a flow rate, a direction of flow, and the like of the fluids flowing through the valve device of the invention.

In a preferred embodiment, the method further includes the application of a defined force and/or of a defined displacement to an upper side of the valve insert in order to switch the valve insert.

In accordance with the above explanations, the intentional or "defined" force and/or the intentional or "defined" displacement may be applied as a function of the desired or required valve state of the valve insert.

The actuation of the valve device particularly preferred in accordance with the invention is a path-oriented one. Nevertheless a force-oriented actuation is equally encompassed by the present invention.

In a further preferred embodiment, the force and/or the displacement are applied to the upper side of the valve insert by means of transmission members.

In a further preferred embodiment, the force and/or the displacement are applied to the valve insert across a cover means, for example a film element.

In a further preferred embodiment, the force is a pressing force which is introduced into a treatment apparatus by installing a valve device of the invention or an external functional means comprising a valve device of the invention.

In a further preferred embodiment, the displacement is introduced by installing a valve device of the invention or an external functional means comprising a valve device of the invention into the treatment apparatus.

Suitable treatment apparatuses may be medical-technical treatment apparatuses such as, for example, a blood treatment apparatus, for instance a dialysis apparatus, a hemodialysis apparatus, an apparatus for hemofiltration or for hemodiafiltration, and the like. They may further include apparatuses in laboratory technology such as analytic apparatuses, for instance chromatography apparatuses, scales etc., apparatuses in food and/or drug production, or the like.

Alternatively, the forces on the valve device may also be forces resulting from the flow of fluids passing through the valve device.

As all of the advantages that may be achieved with the valve device of the invention may also undiminishedly be achieved with the method, reference is made to the corresponding description thereof in order to avoid repetitions.

In order to achieve the object of the invention, the present invention proposes the manufacture of a valve device of the invention by a manufacturing method. The method includes positioning a valve insert above a reception means and positioning the valve insert in the reception means with the aid of a guiding means.

Positioning of the valve insert may be effected by using a machine or a machine control, for example with the aid of a robot. Suitable control or regulation means may be provided.

Insertion of the valve insert in the reception means may be performed while the valve insert is being held at its upper side by a suction cup on an insertion device during insertion.

It is, of course, possible to use any other suitable apparatus for positioning and/or inserting of the valve insert, and the invention is not restricted to the examples given herein.

Furthermore an external functional means may be manufactured by a manufacturing method that includes manufacturing a housing element of at least one thermoplastic material or duroplastic or thermosetting material, forming a reception means in the housing element, inserting a valve insert, and applying a cover means on at least one portion of an upper side of the housing element.

The manufacture of the housing element may be performed, for example, by means of injection molding.

Shaping the reception means may be performed upon manufacturing the housing element, for example by means of finished-casting or injection molding techniques. It may, however, also be performed after manufacturing the housing part by machining of the reception means such as, for example, by milling, grinding, and the like.

The invention equally encompasses to provide or preform a recess suited for receiving the reception means in the housing element and inserting or fitting a separately manufactured reception means in the recess in a suitable manner. A separately manufactured reception means may be connected frictionally and/or by form closure and/or by material connection to the housing element or the hard part, respectively, of the external functional means, for example by bonding, welding, interlocking, toothed engagement, and the like.

The valve insert may be inserted in the reception means from the open side of the external functional means.

Subsequently, a coupling portion of the external functional means having the form, e.g., of a coupling plane may be welded with the cover means, for instance a film.

The valve insert may be positioned inside the external functional means under the film such that it may be pushed into the reception means to different and in particular predetermined depths by an actor pressing down on the cover means at different defined stages of path and/or force of the actor. Different defined, elastic states of deformation of the valve insert may thus result. These may bring about different defined flow rates of the fluids passing through the valve device.

Another method of the invention relates to the preparation of an external functional means for sterile utilization by a method that includes the manufacture of an external functional means as described in the foregoing by means of examples, and the sterilization of the external functional means obtained through the manufacturing method.

The external functional means comprises a valve device of the invention, the valve insert of which is placed in the sterilization state that is in particular provided for this purpose. The sterilization state may be a flow-through position in which the first sealing means does not rest on the second sealing means. Thus, a bidirectional flow of the fluids passing through the valve device of the invention may advantageously be possible. Such a position may be suited particularly well for sterilization of the external functional means.

Sterilization the external functional means may be performed with the aid of a steam/vapor method, a vapor-vacuum method of the ethylene oxide type, or the like. The invention is expressly not restricted to these sterilization methods which are just given by way of example. An appropriate sterilization method may be selected in each single case as depending on the purpose of use of the external functional means and in accordance with the demands to sterility of the external functional means.

Following sterilization, the valve device may in a further preferred embodiment of the method of the invention be brought into a locked position.

The locked position may be a position in which the valve device is merely protected against penetration of impurities, however no external force and/or bias is acting on the valve insert of the valve device. The valve insert may be clamped in the reception means, wherein the self-adjustment of the initial clearance is advantageously not impeded.

The external functional means may be stored in this position.

Preferably, the locked position is identical with the position the valve insert automatically adopts during its insertion upon the manufacturing process. This position may advantageously prevent a valve insert installed in a cassette from falling out upon rotation of the cassette during manufacture and sterilization, storage, transport and/or during a treatment.

The locked position is preferably identical with the sterilization position (vapor sterilization position) and/or with the shipping position, but is, however, not identical with a position wherein a cover member or a pressing door of the treatment apparatus is closed.

The present invention further also proposes an external functional means for sterile utilization, which was sterilized by the method described in the foregoing.

Such an external functional means may, for example, be employed in a medical-technical and/or a laboratory-technical method or for the production of foods and/or drugs. Examples thereof encompass a use of external functional means with a treatment apparatus as described in the foregoing while making reference to the treatment apparatuses themselves.

The external functional means may be a blood treatment cassette having blood-conducting passages for an extracorporeal blood treatment, wherein the valve device is provided and adapted as an intermediary for the introduction of substituate and/or one or several drugs into the blood-conducting passages.

The present invention furthermore also proposes a treatment apparatus comprising at least one valve device of the invention and/or an external functional means. Such a treatment apparatus may, for example, be configured as a blood treatment apparatus.

As the valve device of the invention represents an essential element of any further embodiments and configurations in accordance with the invention, all the advantages achievable with the valve device undiminishedly result for all further aspects and possibilities of use and application thereof.

Fluid-conducting means such as external functional means may generally be delivered in such a way that all of the spaces and surfaces that may be wetted by the fluids during later use are free from pollutants and sterile and remain hermetically tight against the atmosphere. This can usually be effected by pressing housing elements against each other or by elastomer seals or by welding the housing components with each other. Films may equally fulfil the task of the housing elements and may be made fluid-tight against other housing elements by use of pressing or welding.

Advantageously, by choosing suitable geometrical configuration, the elastic valve insert of the valve device of the invention may represent different valve functions (e.g., "sterilization", "open", "closed", "regulating", "check valve") in only one element.

Particularly in the position of a check valve function, the elastic valve insert may advantageously require lower complexity of assemblance due to its geometrical configuration, for example in comparison with the known check valves that are to be assembled in a biased condition.

As a result of using the valve device of the invention, installation spaces and driving means for the valve device may be realized in a space-saving and cost-effective manner, which may provide the above-mentioned functions in a new, safe, simple, and/or cost-saving manner.

Advantageously, the elastic valve insert can for the first time combine the functions of several valve types in one component part and with the requirement of only one single structural space. In order to utilize these valve types, it is not necessary to physically change or exchange a valve device of the external functional means or to provide a plurality of valves. Advantageously, only a corresponding variation of the adaptation or of the control or regulation of the treatment apparatus for operating the valve and for switching over between different valve states is rather sufficient.

Passively operating check valve elements that are known from the prior art are generally installed in the single-use part housing elements in a fixed and biased manner. They are, for example, snapped under bias into retaining bores of hard housing elements or clamped between two hard housing elements (for instance the mushroom-shaped "umbrella valves" by the company Minivalve International, The Netherlands, http://www.minivalve.com).

During sterilization treatments under elevated temperature, and in general due to storage, these elastomer components may partly lose their bias and thus the desired function. Moreover, these elements may inhibit the fluid passage in both directions up to a particular differential response pressure in the one direction and against the maximum particular differential pressure of the fluid system in the other direction. Accordingly, it is possible that a sterilization with sterilization methods requiring a flow through the fluid spaces will in many cases be impossible or only be possible with restrictions (for instance vapor vacuum sterilization or ethylene oxide sterilization). A vapor vacuum sterilization of external functional means—particularly single-use parts of films and hard parts—including semi-open fluid passages adapted to be closed by the films may frequently result in deep-drawing effects involving destruction. Thus, for example, the films heated to their limit of plasticity may be drawn into the semi-open fluid passages upon change from vacuum to overpressure. This may in particular be the case when the check valves have to be arranged so as to close the only fluid inlets of the passages situated on the inner side of the film.

In contrast to fixedly installed and biased check valve devices from the prior art, the valve device of the invention may advantageously allow a flow-through of fluids in both directions during a sterilization process. This may be of particular advantage when sterilization methods requiring a flow through fluid spaces are utilized.

Furthermore, it may advantageously be possible to perform sterilization in a more simple and/or reliable manner. Here, it is possible to use particularly low-cost elastic materials for the valve insert which, due of their biased condition, could previously not be used at all or only by accepting sterilization losses due to lack of durability under certain sterilization conditions.

It may advantageously be possible that suitable elastic materials do not have to include elastomers possessing a particular resistance against creep deformation any more, such as high-priced silicone which implies a technically complex manufacture.

Under treatment conditions, fixedly biased check valves of the prior art may prevent a fluid flow in the opposite direction, whereby particular treatment programs and initial integrity test programs of the single-use part system can frequently not be performed.

With the valve device of the invention, the fluid passage may advantageously be opened and closed at will by the machine control without having to additionally provide any further fluid control elements arranged in parallel or in series for this purpose. The valve device of the invention may thus advantageously contribute to a reduction of construction spaces and/or dead spaces.

The valve device of the invention may for the first time advantageously allow a manufacturing process, treatment and storage that allows flow and is not subjected to any mechanical stress. Here, it is sufficient if the valve device of the invention—other than conventional valve devices—is brought into a biased valve state solely when being installed in the treatment apparatus.

The capability of the valve device to also be brought into an open state and in a closed state by machine control in addition to its check valve function, may advantageously admit an increase of procedural options in fluid arrangements.

By using the valve device of the invention as a multi-stage or continually operating, passively acting, or actively alterable pressure or volume flow control valve, it is advantageously possible to save costs, constructional complexity, as well as installation space.

The valve device of the invention is a multi-function valve device which may advantageously be suited both for the immediate use in repeatedly usable treatment apparatuses as well as in single-use, hermetically insulated disposable arrangements in laboratory-technical and medical-technical fields of application.

The external functional means of the invention may fulfil many different functions. It may be configured cost-efficiently for reception of the valve insert. Particular constructional measures are not necessary for this purpose.

As the valve device of the invention is in a sterilization valve state, i.e., a state without any bias, during its manufacture and storage, an effective flow through critical areas of an external functional means comprising such a valve device is advantageously possible, particularly in sterilization methods according to the method of the type of alternated overpressure and negative pressure. In the check valves customarily installed in a biased and thus closed condition, such critical areas might either not be accessible for treatment fluids or only be rinsed ineffectively due to blind bore arrangements which can not sufficiently be sterilized.

As the valve device of the invention is disposed without any bias or pre-load or pre-stressing during its sterilization and storage, the mechanical dimensions and elastic properties of the valve insert may advantageously fully and in full quality be preserved until the time of its utilization.

The load-free storage of the valve insert may moreover advantageously allow for the use of particularly low-cost thermoplastic elastomers instead of the elastomers that are usually necessary (as silicone rubber in the medical-technical field).

Furthermore, the utilization of thermoplastic elastomers may advantageously allow for new constructional possibilities. A thermoplastic/elastomer mixture for the valve insert which includes both elastomers and the thermoplastic materials usable for the housing elements, may be connectable to the housing elements in a suitable, advantageous and/or improved manner.

Thus, it may, for example, advantageously be possible to provide welds between the elastic valve elements and the thermoplastic hard housing elements for assemblance purposes and sealing the valve element against the housing.

Installation of the external functional means in the treatment apparatus not only allows to provide the correct position, support and fluid-tightness of the external functional means. In contrast to conventional arrangements including biased check valves, it is advantageously possible with the valve device of the invention to omit additional fluid passages—e.g. fluid passages arranged in parallel—having additional machine-operated valves for opening the fluid arrangement bidirectionally for the through flow. Thus, it is advantageously possible not only to save installation spaces and manufacturing costs in the machine or treatment apparatus and in the external functional means, but also to avoid undesirable dead flow spaces.

The capability of admitting tolerances in the installation and coupling of the external functional means in the treatment apparatus may advantageously avoid functional impairments of the single component parts. It moreover contributes to low-price production costs.

Apart from this, it is advantageously possible to examine the valve functions of the valve device of the invention in a simple and easy manner by machine-controlled routines prior to beginning the proper treatment tasks. Such examination may, for example, be an air pressure test which may simply and easily be performed by opening the valve device of the invention, pressing a test fluid into a compressible space against the direction that is possible in conventional check valves, and then bringing the valve device of the invention into a check valve position.

As the axial, elastic seat region of the valve insert and/or of the elastic sealing ring may be realized with a defined resilience, it may advantageously be possible to realize a pressure control unit or volume flow control unit that is fixedly set or adjustable according to need at low cost.

The freedom of geometrical design of the axial elastic seat region and/or of the elastic sealing ring under the aspect of the rigidity thereof may advantageously allow to advantageously set the progressivity of the spring rate of the elastic sealing means in the pressing situation of the valve device within wide margins.

Driving the valve may in a preferred embodiment predominantly be performed in a path-oriented manner, wherein the fact that the predetermined deformations naturally also imply forces such as, e.g., reset forces and biases, is of less or no importance. The latter ones are negligible as they may be very small, e.g., due to construction properties. It is rather the defined impression of path which offers considerable advantages compared with the presetting of forces, which is alternatively possible in accordance with the invention. Thus, due to inevitable force tolerances and other imponderabilities, accurately observing low-quantity forces is substantially more complex and unreliable than observing path impressions and displacements. An important advantage of the valve device of the invention resides in the circumstance that the path alterations may be observed accurately in a simple manner. In this regard, even overall tolerances (e.g., with regard to the valve body) may be compensated in a reliable manner.

An elastic mode of construction of the valve insert may advantageously result in enhanced insensitivity to tolerances with regard to tolerances of impression of path.

Advantageously, this may in particular allow the realization of the valve device as a constant volume flow regulation valve that is fixedly set (by way of installation). The valve device may thus advantageously be realized as a simple and passively acting arrangement that is capable of altering the passage resistance as a function of volume flow, which may lead to a regulation of the volume flow in accordance with the principle of a proportional control unit.

Whenever "fluids" are mentioned in the context of the present invention, the present invention will alternatively also encompass precisely one fluid or one mixture whenever it is recognizable to the skilled person that the respective statements may also apply to a single fluid or to mixtures of fluids. The reverse case is also encompassed by the present invention.

Here it should be noted in the context of the present disclosure that the expressions "may comprise", "may be", and the like are synonymous with the expressions "preferably comprises", "is preferred" and the like, that are equally used here and elsewhere.

Further features and aspects of example embodiments of the present invention are described in more detail below with reference to the appended Figures.

DETAILED DESCRIPTION

Figure 1:
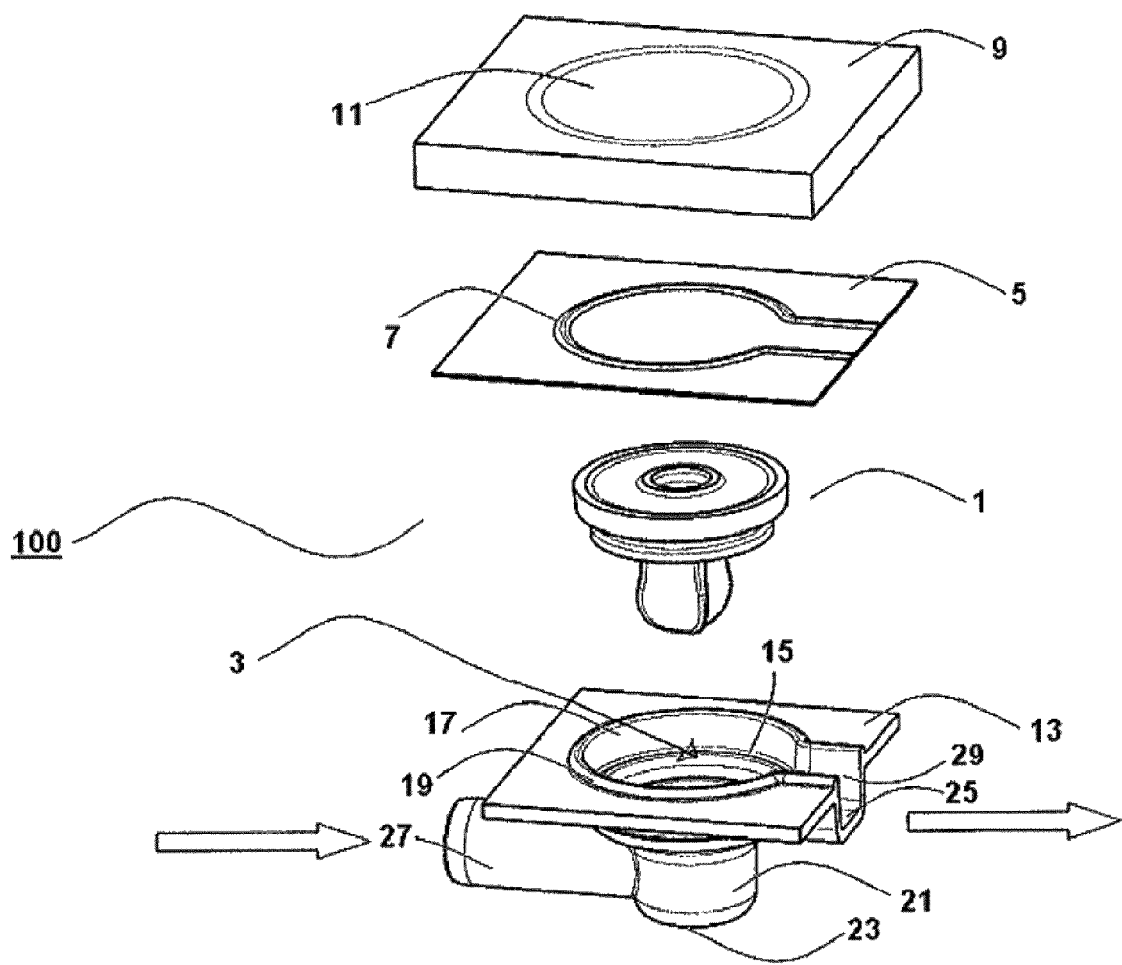
FIG. 1 shows an exploded view of components of a valve device in accordance with the present invention.

In the following, the valve device of the invention shall be described by way of preferred embodiments thereof while making reference to the drawings. In the figures of the drawing, same reference symbols designate same or identical elements, wherein:

In accordance with the exploded view of FIG. 1, the valve device 100 comprises a valve insert 1 being inserted into a reception means 3. The valve insert 1 is covered at its upper side by a cover means, for example a film element 5, which comprises a static sealing strip 7.

In accordance with the invention, the sealing strip 7 may be configured, e.g., in the shape of a sealing ring or seal rim, a dent, or the like.

Above the film element 5 a transmission member 9 is arranged which comprises a movement transmission means 11 for transmitting movements or forces in the axial direction of the valve insert (in FIG. 1 a direction "from top to bottom") or vice versa.

The transmission member 9 may be arranged on the machine side, i.e., it may be part of a treatment apparatus not shown in FIG. 1 such as, for example, a treatment apparatus for treating blood.

The reception means 3 is provided in a housing element 13. As is shown in FIG. 1, for instance, the housing element 13 may be part of an external functional means (not shown).

The housing element 13 may be made of a stiff or comparatively stiff material such as, for example, a thermoplastic material.

The reception means 3 comprises a second sealing means having the form, for instance, of a rigid sealing ring 15 as well as an upper seat bush 17, a static sealing ring 19, and a lower seat bush 21. The lower seat bush 21 has a rigid front end portion 23.

The rigid sealing ring 15 of FIG. 1 exemplarily has an undulating, i.e., slightly curved, configuration.

The reception means 3 further comprises a partly semi-open flow passage 25 for the fluids passing through the valve device 100 such as, for example, blood and/or substitute liquid and/or sterilizing liquid. The flow passage 25 includes flow passage portions 27 and 29. In FIG. 1, the flow passage portion 27 is shown as an inflow passage and the flow passage portion 29 as an outflow passage, as is indicated by the arrows. However, the valve device 100 may also be flushed in a different direction, in particular in the reverse direction.

The valve insert 1 may open or close the flow passage 25 depending on the mode of function, wherein the valve insert 1 correspondingly adopts one of the valve states described in the foregoing and also represented in the following by way of the figures.

Figure 2:
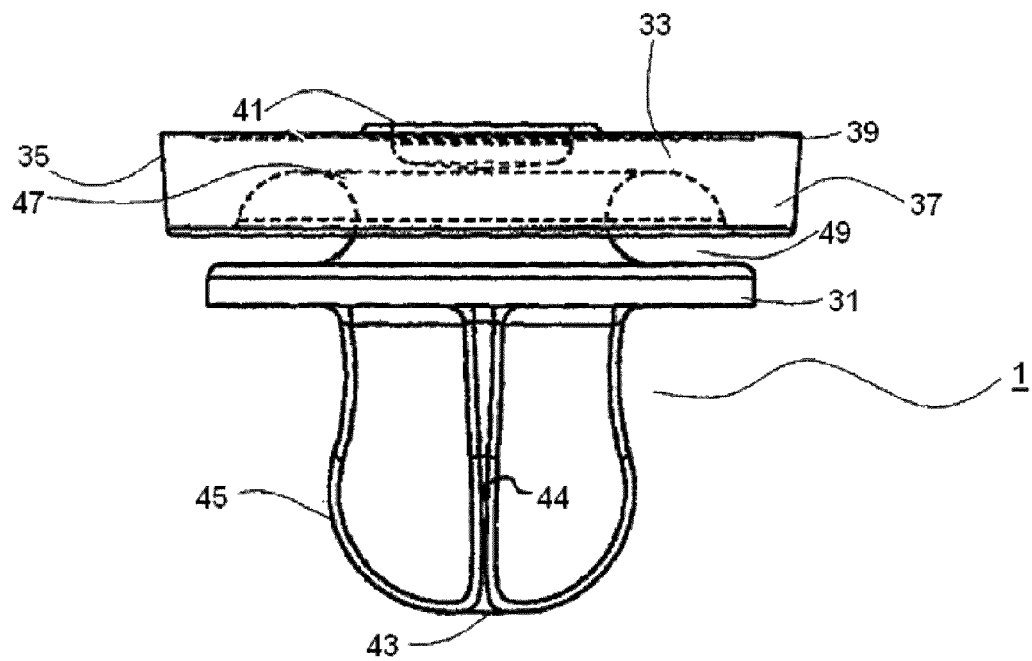
FIG. 2 shows a schematically simplified lateral view of a valve insert of a valve device in accordance with the present invention.

FIG. 2 shows a schematic lateral view of a valve insert 1 of a valve device 100 of the invention in a partly cut-open representation.

The valve insert 1 comprises a first sealing means having, for instance, the form of an elastic sealing ring 31, a bending ring region 33, as well as a guiding means having, for instance, the form of guide ribs 45. Furthermore a static valve seat 35, an elastic seat region having the form of an elastic seat region 37, an outer front ring region 39, an inner front ring region 41, and an front end stop 43 are shown.

The elastic sealing ring 31 has a planar, i.e., flat configuration at its lower side (i.e., at the bottom in the representation of FIG. 2).

Upon application of an axial displacement and/or an axial force, in particular a pressing force, to the inner front ring region 41, a compression zone 47—e.g., a zone of axial compression—of the valve insert 1 may undergo elastic deformation, e.g., compression. FIG. 2 shows a deformation space 49 whose shape and volume are variable depending on the valve state of the valve device 100.

Figure 3:
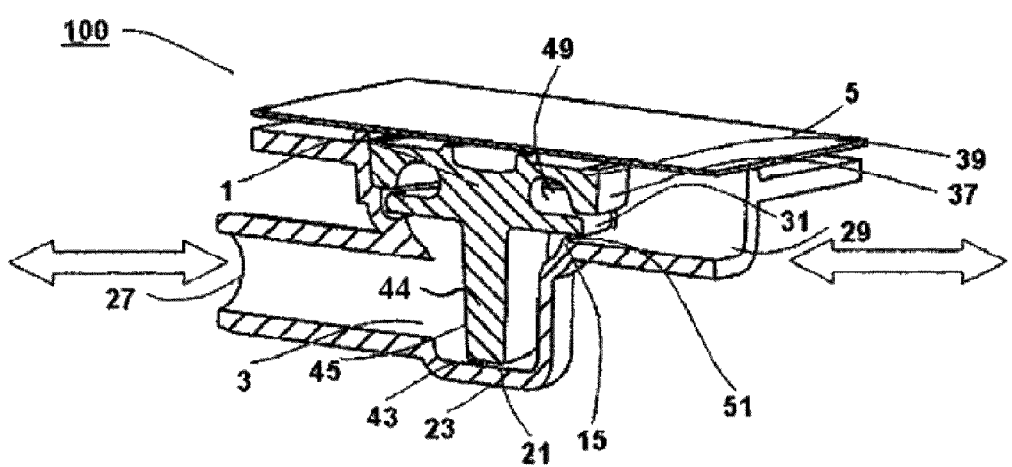
FIG. 3 schematically shows a sectional, lateral view of a valve device in accordance with the present invention in a valve state of a sterilization or storage position.

The above-mentioned central region is exemplarily shown in FIG. 3 designated by reference numeral 44. As is visible in FIG. 2, the accumulation of material of the central region 44 may be effected, e.g., by the convergence of guide ribs 45 in an axis of symmetry of the valve insert 1.

FIGS. 3 to 7 show different, exemplarily selected valve states of the valve device 100 that may be obtained by applying a displacement and/or a force such as, for example, a pressing force on the part of a treatment apparatus or a force of a fluid to the valve insert 1. The valve insert 1 is adapted to be switched between the valve states by applying or releasing the force. FIG. 3 shows in a schematically simplified manner a sectional view of the valve device 100 in a valve state that will in the following be referred to as a sterilization or storage position.

The valve insert 1 is placed inside the reception means 3. The valve insert 1 contacts the rigid front end portion 23 of the lower seat bush 21 of the reception means 3 through its guide ribs 45. The valve insert 1 is covered by the film element 5.

With this design of the bending ring region 33 of the valve insert 1, the frictional connection between the guide ribs 45 (cf. FIG. 2) and the inner wall of the lower seat bush 21 of the reception means 3 preferably is advantageously just sufficient to securely prevent the valve insert 1 from falling out due to its own weight.

The bending ring region 33 is preferably adapted such that a transient axial displacement—for example upon assemblance—of the front end stop 43 of the valve insert 1 to the bottom of the lower seat bush 21 is advantageously entirely reversed by the reset force of the bending ring region 33. Here, the reset forces of the bending ring region 33 preferably overcome the frictional forces between the guide ribs 45 and the inner walls of the lower seat bush 21 or the guide bush of the reception means 3. In this way, a particularly simple assembly may advantageously be ensured.

In the sterilization position shown in FIG. 3 no external forces are acting on the valve insert 1. The valve insert 1 is thus substantially not subjected to any bias and/or material stress. All of the regions of the valve insert 1 that are relevant for its main functions are not pressed with either the reception means 3 or the housing element 13 (not shown here). They are free from significant material stresses.

As no forces or displacements are acting on the elastic seat region 37 in FIG. 3, the deformation space 49 of the valve insert 1 takes a maximum volume.

The valve device 100 is in a state which is opened for a fluid flowing through the valve device 100. In this case, the fluids may flow bidirectionally through the valve device 100, as can be seen from the double arrows represented in FIG. 3.

The fluid flow through the valve device 100 takes place through a gap 51 located between the elastic sealing ring 31 of the valve insert 1 and the rigid sealing ring 15 of the reception means 3.

Such a state is particularly well suited for sterilization of the valve device 100 or for sterilization of an external functional means connected to a valve device 100.

As the single components are arranged without any stresses—construction stresses among each other and internal stress as well—in such a valve state, this valve is furthermore preferably suited for prolonged storage of the valve device 100 or of an external functional means including a like valve device 100. A loss of tension and an impairment of the respective component parts associated therewith do not occur in the absence of tension.

The open sterilization position of the valve device 100 may now allow to perform any sterilization or other preliminary treatments that require the free bidirectional passage of sterilization or treatment fluids such as, for example, blood and/or substitute liquid, through the flow passage 25.

Figure 4:
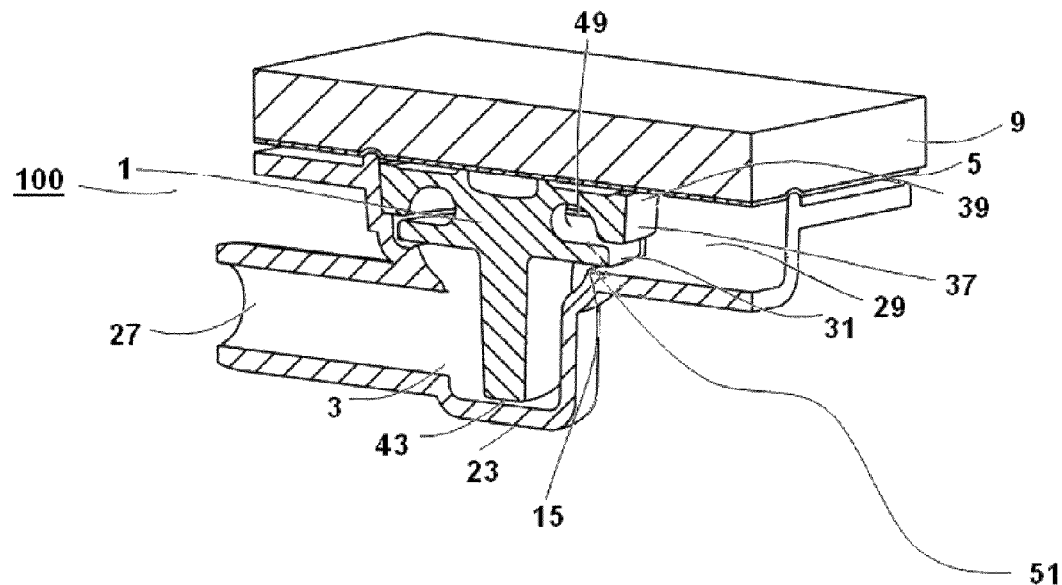
FIG. 4 schematically shows a sectional, lateral view of a valve device in accordance with the present invention in a valve state of a permanently opened valve position.

FIG. 4 shows in a schematically simplified manner a lateral view of the valve device 100 of FIG. 3 in a permanently opened valve position as the valve state. In contrast to the representation of FIG. 3, the valve device 100 in FIG. 4 is arranged inside a treatment apparatus. This may be recognizable from the fact that a transmission member 9, for example a pressure actor of a treatment apparatus, is arranged above the film element 5.

The valve insert 1 is held between the reception means 3 and the transmission member 9 by means of the guide ribs 45 and through the intermediary of the outer front ring region 39.

The transmission member 9 may be adapted such that a bidirectional flow through the valve insert 1 is possible in the permanently opened valve position. The valve device 100 is thus in an opened position, either inherently due to its presence inside the machine, or due to machine control.

The transmission member 9 rests on the film element 5 such that a closure between film element 5 and outer front ring region 39 is obtained, which is different from the position shown in FIG. 3 in which a space between film element 5 and outer front ring region 39 is kept open for the purpose of sterilization.

Figure 5:
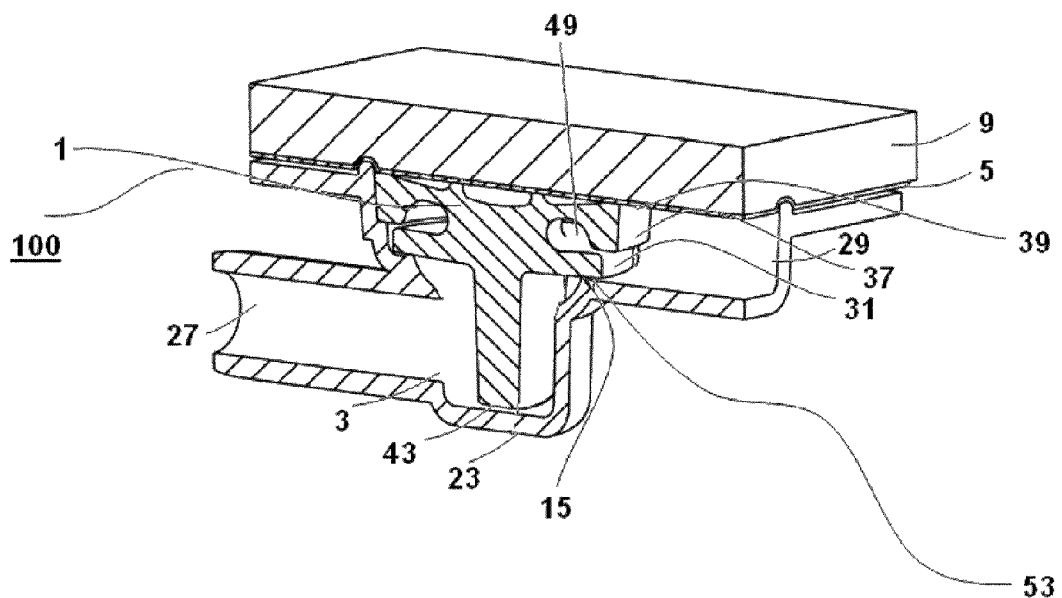
FIG. 5 schematically shows a sectional, lateral view of a valve device in accordance with the present invention in a valve state of a closed check valve.
Figure 6:
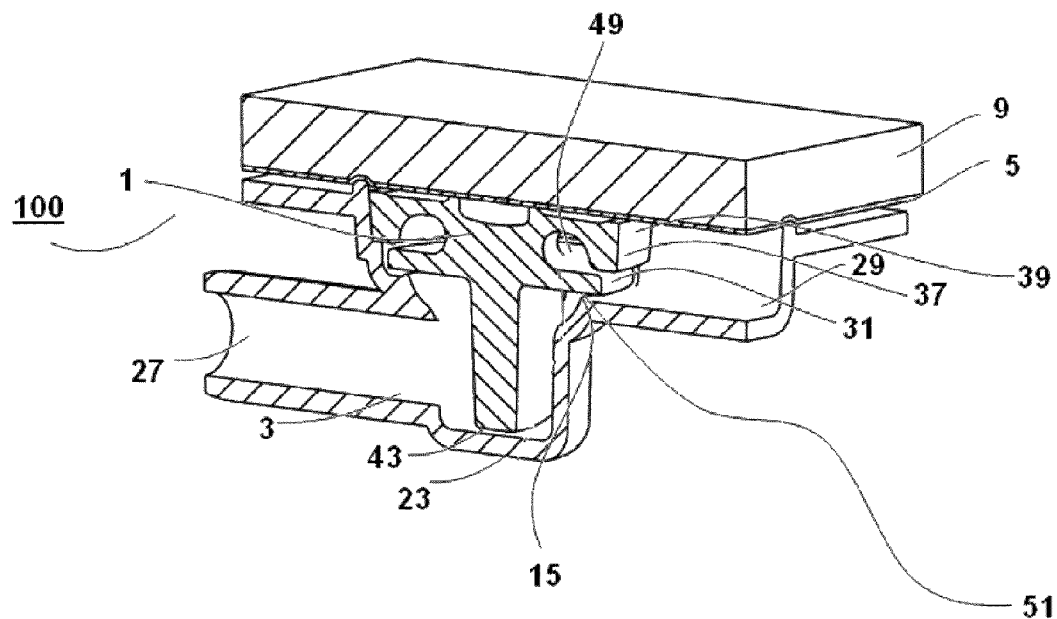
FIG. 6 schematically shows a sectional, lateral view of a valve device in accordance with the present invention in a valve state of an opened check valve.

FIGS. 5 and 6 show in a schematically simplified manner lateral views of the valve device 100 of FIGS. 3 and 4 in a valve state of a closed check valve (FIG. 5) and in a valve state of an opened check valve (FIG. 6), respectively.

In FIG. 5, installation pressing of the valve insert 1 is enhanced by shortening a path distance (in the axial direction, i.e. in the direction "from top to bottom" in FIG. 5) between the reception means 3 and the transmission member 9, and is then kept constant. In passive machine arrangements not provided with active valve functions, this may done solely by placing the external functional means inside the machine. In active machine arrangements having additional open/close functions of the valve devices 100, this may be done by driving the transmission member 9 correspondingly.

FIG. 5 shows the biased, closed valve state of the valve device 100 when a fluid present accumulates against the passing direction at the rigid sealing ring 15, or when the fluid accumulates in the passing direction, however the pressure difference between the inflow and outflow sides is still smaller than the adjusted minimum response pressure of the check valve.

In a contact/pressing region 53 the elastic sealing ring 31 and the rigid sealing ring 15 rest on each other or are pressed against each other.

FIG. 6 shows the valve state during a flow through the valve device 100 in the passing direction. Particularly in this valve state, the above-described compensation of tolerances may be effected in the axial direction between the inner front ring region 41 and the front end stop 43 and ensures constant functional properties. In the check valve position, the front end stop 43 of the valve insert 1 is then already placed at a stop against the rigid front end portion 23 of the lower seat bush 21.

A gap 51 remains between the elastic sealing ring 31 and the rigid sealing ring 15.

Figure 7:
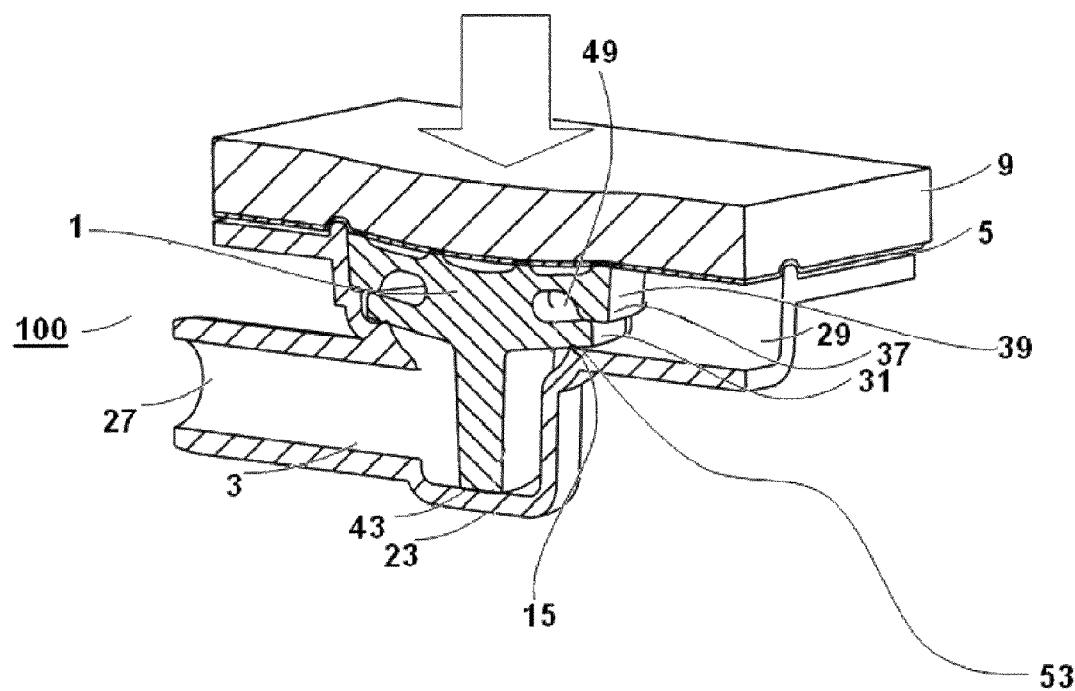
FIG. 7 schematically shows a sectional, lateral view of a valve device in accordance with the present invention in a valve state as a permanently closed valve or as a control valve.

FIG. 7 shows in a schematically simplified manner a lateral view of a valve device 100 in a valve state as a permanently closed valve or as a control valve. Such a control valve may act as pressure or volume flow control valve.

In this valve state, the transmission member 9 enhances pressing in the axial direction (which refers to a direction extending vertically downward from above in the figure) to a larger extent of axial displacement until the outer front ring region 39 enters into mechanical pressing contact with the elastic sealing ring 31 in the axial direction.

In this way, pressing between the elastic sealing ring 31 and the rigid sealing ring 15 is increased to such a degree that the valve device 100 is closed bidirectionally against the pressure difference resulting from construction.

In the valve state shown in FIG. 7, the valve device 100 of the invention may act as a pressure or volume flow control valve.

When the seat region 37 of the valve insert 1, which is elastic in the axial direction, or the elastic sealing ring 31 associated as a contact mate are adapted to have a defined resilience, e.g. by providing it/them with an additional groove or with resilient, thin annular bars or knobs which effect an intended contact between the axial elastic seat region 37 and the elastic sealing ring 31 in the event of the further axial deflection of the valve insert 1 mentioned above, then a definitely higher bias of the valve device 100 may result in this valve state.

Such a higher bias may either take place in two discrete stages (gap 51 between axial elastic seat region 37 and elastic sealing ring 31) before axial actuation and contact after axial actuation or in a continuous manner (initial contact between the named partners), in a path-dependent manner depending on the axial displacement of the transmission member 9.

Figure 8:
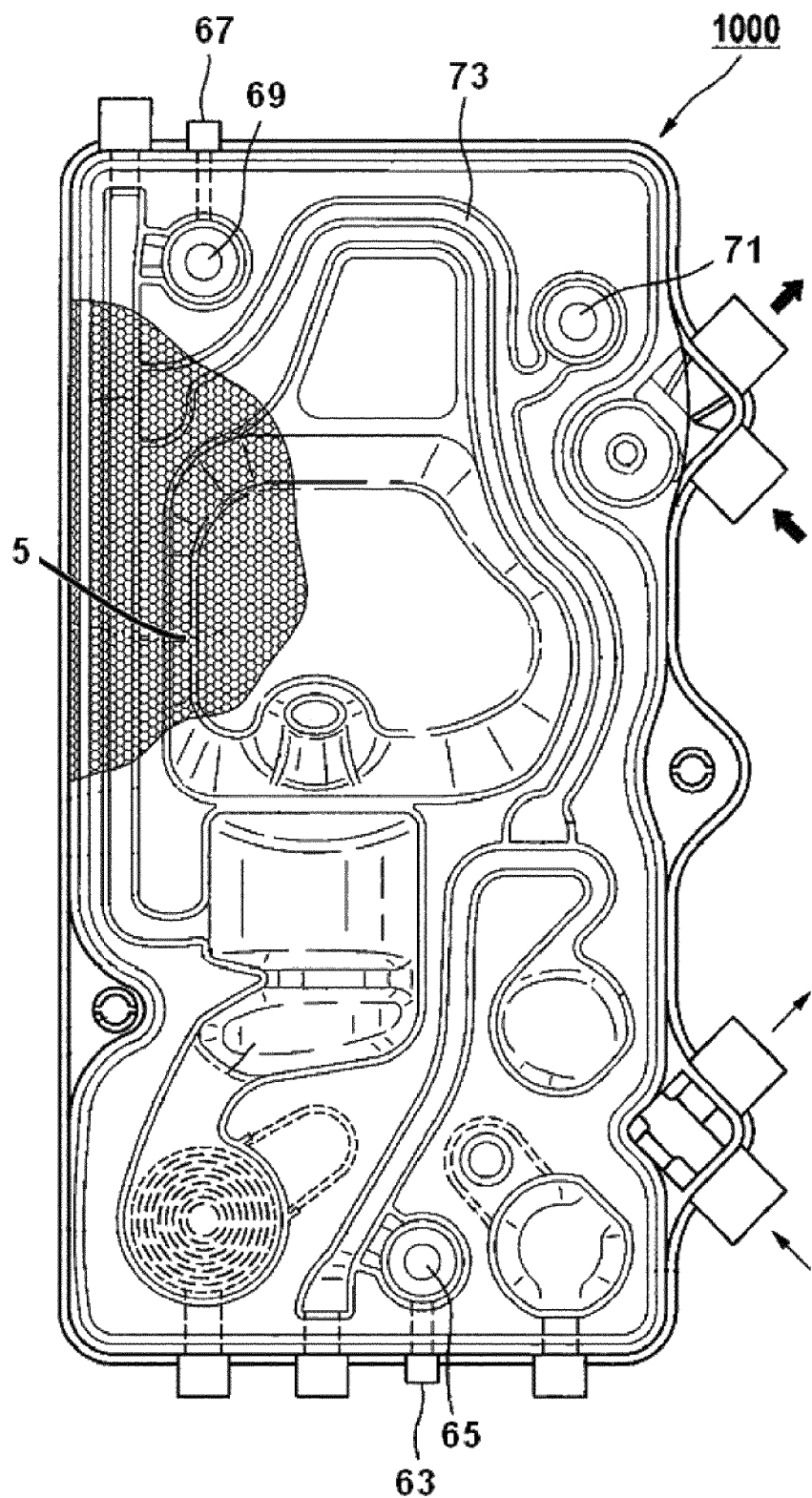
FIG. 8 shows a lateral view of an external functional means of the invention in accordance with a preferred embodiment, which is provided with a cover means at its front side.

FIG. 8 shows a lateral view of an external functional means which is provided with a cover means at the surface which one looks upon in FIG. 8.

Here, the external functional means is exemplarily configured as a blood treatment cassette 1000 having chambers, passages, valves, and the like. The blood treatment cassette 1000 of FIG. 8 is provided at its front side with a cover means, in the present case examplarily a film 5 as already specified in the foregoing.

The blood treatment cassette 1000 may be coupled, at least by the front side shown in FIG. 8, to a blood treatment apparatus (not shown in FIG. 1).

The blood treatment cassette 1000 comprises an arterial heparin addition site 63. Here, it should be noted that the heparin addition site 63 may also be suited and intended for adding other pharmacological active agents than heparin, which are only in a preferred manner anti-coagulants or combinations of active agents. This should also be considered whenever heparin is mentioned before or afterwards in any kind of context.

The blood treatment cassette 1000 comprises a check valve 65 of the arterial heparin addition site 63. The check valve 65 is a practical example of the valve device of the invention of the present application.

The blood treatment cassette 1000 further includes a check valve 69 for a venous heparin addition site 67.

By actuating a check valve 71 as another embodiment of the valve means of the invention, substitute may be introduced into a substitute conduit 73.

Figure 9:
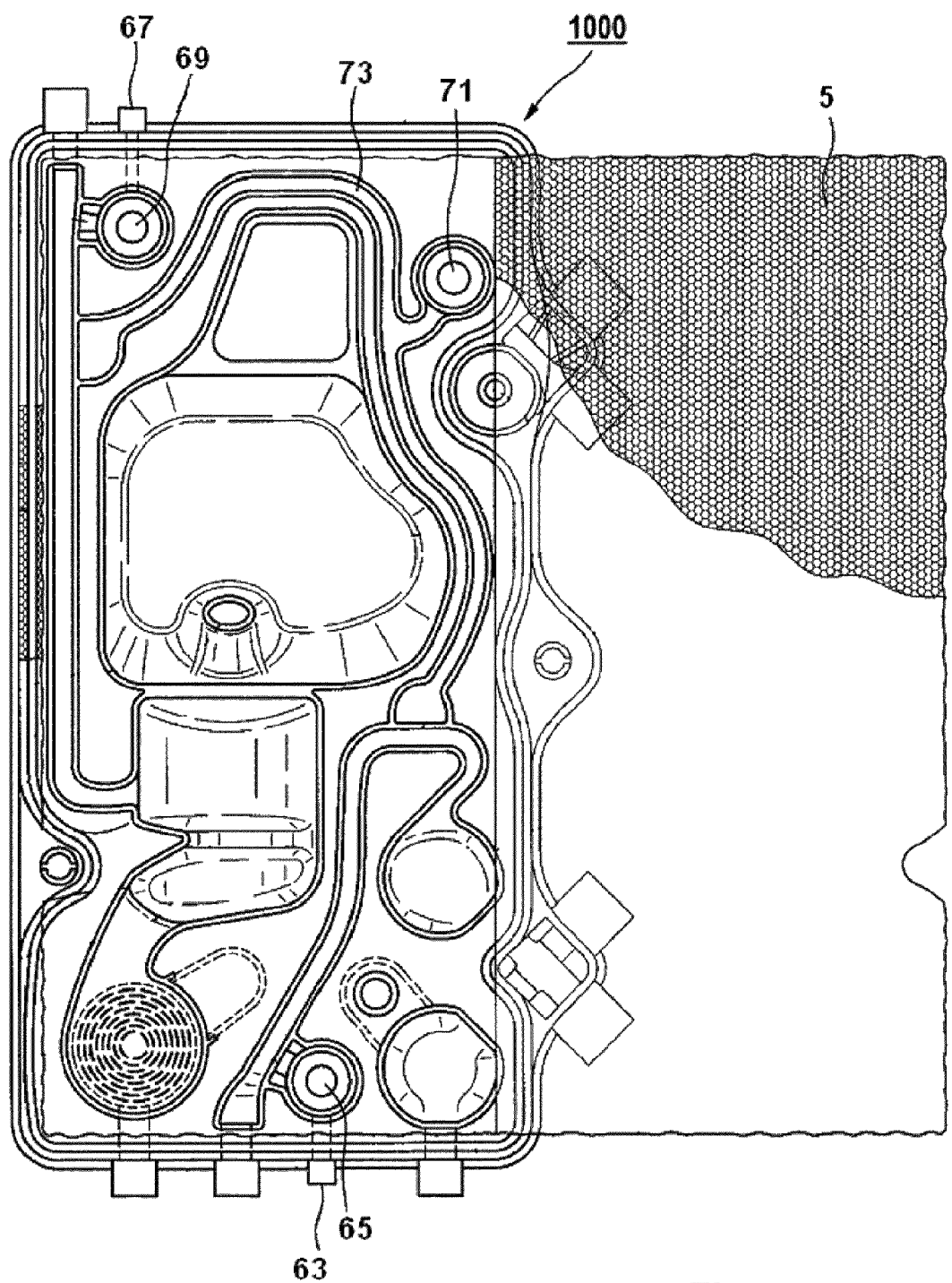
FIG. 9 shows the external functional means of FIG. 8 with a cover means having been opened.

FIG. 9 shows the blood treatment cassette 1000 of FIG. 8, wherein the film is shown as cut open at the left margin of the blood treatment cassette 1000 as well as at the top and bottom and having been opened to the right.

FIG. 9 shows the elements inside the blood treatment cassette 1000 which are visible in more detail after having cut open the film.

In order to avoid repetitions, reference is made to the configurations of the individual elements discussed in the foregoing in the description of FIG. 8.

Figure 10:
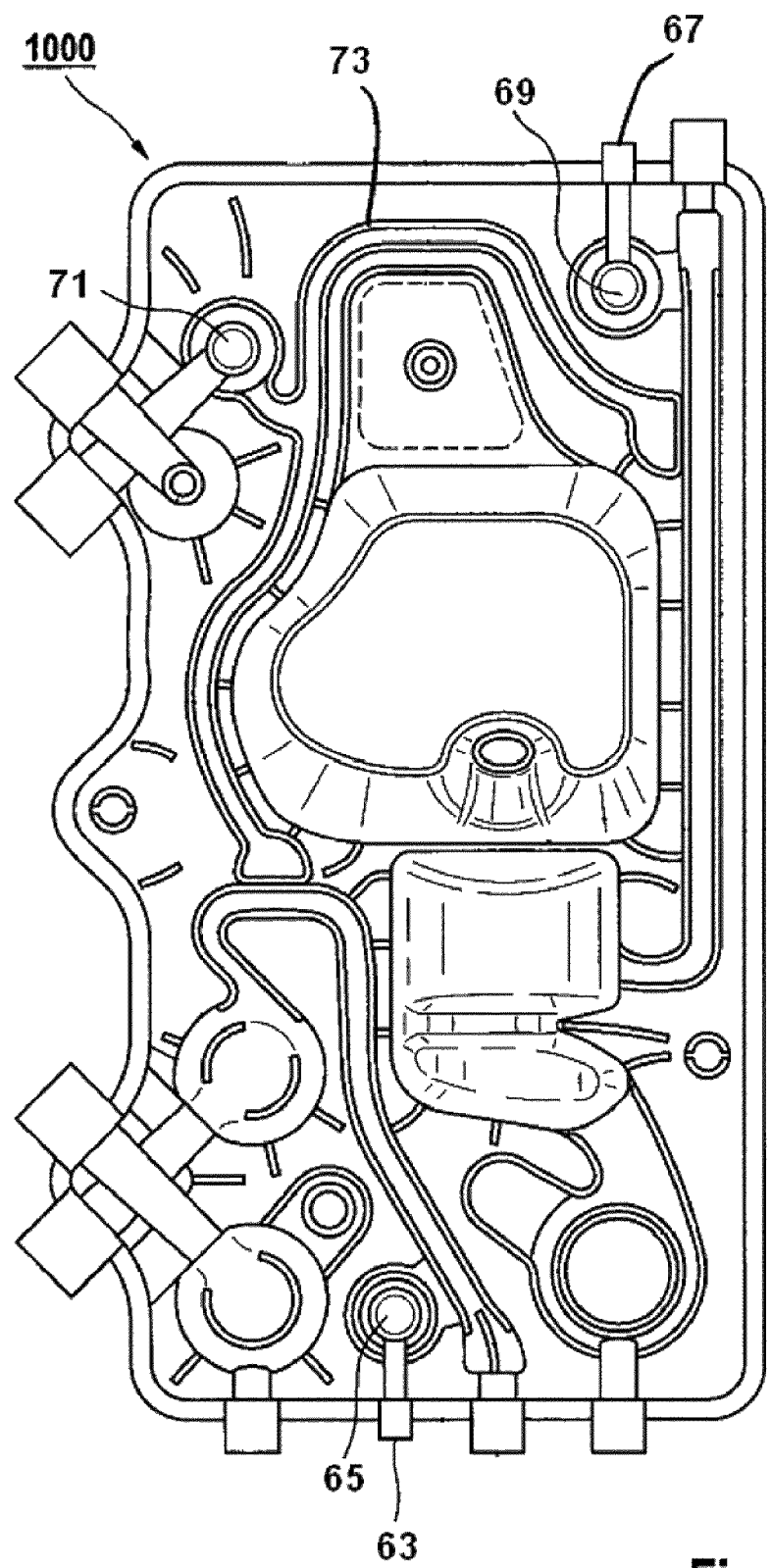
FIG. 10 shows the external functional means of FIG. 8 and FIG. 9 from its rear side.

FIG. 10 shows the blood treatment cassette 1000 from its rear side. When the blood treatment cassette 1000 is coupled to the blood treatment apparatus, an observer opening a door of the blood treatment apparatus for removing the blood treatment cassette 1000 will look upon this rear side.

For further details concerning the blood treatment cassette 1000, reference is made to its detailed description in the above-mentioned application directed thereat.

The following is a List of Reference Numerals used herein:

| Reference numeral | Description |
| --- | --- |
| 100 | valve device |
| 1000 | blood treatment cassette |
| 1 | valve insert |
| 3 | reception means |
| 5 | film element |
| 7 | static sealing strip |
| 9 | transmission member |
| 11 | axial movement transmission means |
| 13 | housing element |
| 15 | rigid sealing ring |
| 17 | upper seat bush |
| 19 | static sealing ring |
| 21 | lower seat bush |
| 23 | rigid front end portion of the lower seat bush |
| 25 | semi-open flow passage |
| 27 | flow passage portion |
| 29 | flow passage portion |
| 27 and 29 | flow passage |
| 31 | elastic sealing ring |
| 33 | bending ring region |
| 35 | static valve seat |
| 37 | elastic seat region |
| 39 | outer front ring region |
| 41 | inner front ring region |
| 43 | front end stop |
| 44 | central region |
| 45 | guide ribs |
| 47 | compression zone |
| 49 | deformation space |
| 51 | gap |
| 53 | contact/pressing region |
| 63 | arterial heparin addition site |
| 65 | check valve of the arterial heparin addition site |
| 67 | venous heparin addition site |
| 69 | check valve of the venous addition site |
| 71 | check valve for substitute conduit |
| 73 | substitute conduit |

What is claimed is:

1. A valve device comprising:
    at least one valve insert which is elastic in at least one portion thereof; and
    at least one reception means for receiving the valve insert, wherein the valve insert is configured such that due to its elasticity it may be switched between at least three different valve states upon an impression of path and/or an application of force, and
    wherein the valve states are selected from the group consisting of an opened functional state of the valve, a check valve state, a control or regulation valve state and a closed valve state.

2. The valve device according to claim 1, wherein one of the at least three different valve states is the opened functional state of the valve.

3. The valve device according claim 1, wherein one of the at least three different valve states is the check valve state.

4. The valve device according to claim 1, wherein one of the at least three different valve states is the control or regulation valve state.

5. The valve device according to claim 1, wherein one of the at least three different valve states is the closed valve state.

6. The valve device according to claim 1, wherein the valve insert comprises an elastomer material at least in a portion thereof.

7. The valve device according to claim 1, wherein the valve insert comprises impressions at least in a portion thereof.

8. The valve device according to claim 1, wherein the valve insert comprises at least one first sealing means provided and adapted for being pressed in at least one portion thereof by form closure and/or frictionally with at least one portion of a second sealing means of the reception means.

9. The valve device according to claim 8, wherein the first sealing means is pressable with the second sealing means by impression of path and/or transmission of force to the valve insert.

10. The valve device according to claim 8, wherein a force acting on the valve insert is a pressing force introduced by installation of the valve device into a treatment apparatus.

11. The valve device according to claim 9, wherein the impression of path on the valve insert is a displacement introduced by installation of the valve device into a treatment apparatus.

12. The valve device according to claim 10, wherein the pressing force is transmitted by a transmission member of the treatment apparatus.

13. The valve device according to claim 11, wherein the displacement is transmitted by a transmission member of the treatment apparatus.

14. The valve device according to claim 1, wherein the valve insert comprises at least one guiding means for introducing the valve insert into the reception means.

15. The valve device according to claim 1, wherein the valve insert comprises at least one elastic bending ring region.

16. The valve device according to claim 1, wherein the valve device is provided with a cover means at least on one upper side thereof.

17. The valve device according to claim 1, wherein the valve insert is switchable across the cover means by a force and/or an impression of path transmitted by a treatment apparatus.

18. An external functional means comprising at least one valve device according to claim 1.

19. The external functional means according to claim 18, wherein the external functional means is configured as a blood treatment cassette having blood-conducting passages for extracorporeal blood treatment, wherein substitute and/ or one or several drugs are introducable into the blood-conducting passages via the valve device.

20. A method of controlling or regulating a passage of fluid, including the step of:
  controlling the valve device according to claim 1 to control or regulate the passage of the fluid.

21. The method according to claim 20, further including the step of:
  applying a defined force and/or a defined impression of path to an upper side of the valve insert for the purpose of switching the valve insert.

22. The method according to claim 21, wherein the force and/or the impression of path is applied to the upper side of the valve insert by a transmission member.

23. The method according to claim 21, wherein the force and/or the impression of path is applied to the valve insert across a cover means.

24. The method according to claim 21, wherein the force is a pressing force or the impression of path is a displacement, and the force and/or the impression of path is introduced by installation of the valve device or of an external functional means comprising the valve device into a treatment apparatus.

25. The method according to claim 21, wherein the force and/or the displacement is a force and/or displacement resulting from the flow of fluids passing through the valve device.

26. A treatment apparatus comprising at least one valve device according to claim 1 and/or an external functional means comprising at least one valve device according to claim 1.

27. The treatment apparatus according to claim 26, wherein the treatment apparatus is configured as a blood treatment apparatus.

* * * * *

UNITED STATES PATENT AND TRADEMARK OFFICE
CERTIFICATE OF CORRECTION

PATENT NO.         : 9,789,300 B2
APPLICATION NO.    : 12/766266
DATED              : October 17, 2017
INVENTOR(S)        : Martin Lauer It is certified that error appears in the above-identified patent and that said Letters Patent is hereby corrected as shown below:

In the Claims

Column 24, Line 12, Claim 3, after "according" insert --to--.

Signed and Sealed this
Twelfth Day of December, 2017

Joseph Matal
*Performing the Functions and Duties of the
Under Secretary of Commerce for Intellectual Property and
Director of the United States Patent and Trademark Office*